(12) United States Patent
Chandler

(10) Patent No.: US 7,772,012 B2
(45) Date of Patent: Aug. 10, 2010

(54) DEVICE FOR DETECTING THE PRESENCE OF HEMOGLOBIN IN A BIOLOGICAL SAMPLE

(75) Inventor: Howard Milne Chandler, Yarmouth, ME (US)

(73) Assignee: Quest Diagnostics Investments Incorporated, Wilmington, DE (US)

( * ) Notice: Subject to any disclaimer, the term of this patent is extended or adjusted under 35 U.S.C. 154(b) by 173 days.

(21) Appl. No.: 11/568,382

(22) PCT Filed: Apr. 29, 2005

(86) PCT No.: PCT/AU2005/000613

§ 371 (c)(1),
(2), (4) Date: Sep. 11, 2007

(87) PCT Pub. No.: WO2005/106498

PCT Pub. Date: Nov. 10, 2005

(65) Prior Publication Data

US 2008/0113382 A1    May 15, 2008

Related U.S. Application Data

(60) Provisional application No. 60/566,731, filed on Apr. 30, 2004.

(51) Int. Cl.
*G01N 33/53* (2006.01)
(52) U.S. Cl. ............... 436/518; 436/514; 436/810; 436/910; 435/287.1; 435/287.2; 435/810; 435/910; 422/56; 422/58; 422/59; 422/61; 422/100

(58) Field of Classification Search ............... 436/514, 436/518; 435/810, 910, 287.1, 287.2; 422/56, 422/57, 58, 60, 61, 100
See application file for complete search history.

(56) References Cited

U.S. PATENT DOCUMENTS

| | | | |
|---|---|---|---|
| 4,310,626 A | 1/1982 | Burkhardt et al. | |
| 4,447,542 A * | 5/1984 | Gantzer ................. | 436/66 |
| 4,683,197 A | 7/1987 | Gallati | |
| 5,081,040 A | 1/1992 | Patel et al. | |
| 5,171,529 A | 12/1992 | Schreiber | |
| 5,602,040 A * | 2/1997 | May et al. ............... | 436/514 |
| 6,221,678 B1 * | 4/2001 | Chandler ................ | 436/530 |
| 6,739,877 B2 | 5/2004 | Bailey et al. | |
| 6,977,173 B2 * | 12/2005 | Chandler ............... | 435/287.1 |

(Continued)

FOREIGN PATENT DOCUMENTS

EP    0 269 362    6/1988

(Continued)

OTHER PUBLICATIONS

Allison J. et al, A comparison of fecal occult-blood tests for colorectal-cancer screening, New England J. Med. (1996) vol. 334(3) p. 155-159.

(Continued)

*Primary Examiner*—Bao-Thuy L Nguyen
(74) *Attorney, Agent, or Firm*—Foley & Lardner LLP

(57) ABSTRACT

A device and method for detecting the presence of hemoglobin in a biological sample, more particularly, the presence of blood in a fecal sample as an indicator of upper or lower gastrointestinal tract bleeding.

10 Claims, 3 Drawing Sheets

U.S. PATENT DOCUMENTS

| | | | |
|---|---|---|---|
| 7,067,264 B2* | 6/2006 | Bagaria | 435/7.21 |
| 2002/0123085 A1* | 9/2002 | Saunders | 435/7.92 |
| 2002/0127525 A1 | 9/2002 | Arington et al. | |
| 2003/0101076 A1 | 5/2003 | Zaleski | |

FOREIGN PATENT DOCUMENTS

| | | |
|---|---|---|
| EP | 0 354 978 | 2/1990 |
| WO | WO 00/29852 | 5/2000 |

OTHER PUBLICATIONS

Citro et al, A Fundamental Metric for Continuity of Care: Modeling and Performance Evaluation, IEEE Transactions on Information Technology in Biomedicine, vol. I. No. 3, Sep. 1997, pp. 189-:204.

International Search Report for PCT Application No. PCT/AU05/000613 dated Jul. 31, 2008.

Krahl. D. Extend: An Interactive Simulation Tool. IEEE. Proceedings of the 2003 Winter Simulation Conference, vol. I, Dec. 2003, pp. 188-196.

Price et al., R.N. Healthcare Simulation Modeling and Optimization Using MedModel, IEEE, Simulation Conference Proceedings, vol. I, Dec. 1999, pp. 215-219.

Vaananen P. et al, The rapid immunological detection of fecal occult blood by use of a latex-agglutination test, Clin Chem. (1988) vol. 34, No. 9 p. 1763-1766.

* cited by examiner

| 1 | 2 | 3 | 4 | 5 | 6 |
|---|---|---|---|---|---|

Figure 1

DEVICE FOR DETECTING THE PRESENCE OF HEMOGLOBIN IN A BIOLOGICAL SAMPLE

FIELD OF THE INVENTION

The present invention relates generally to a device and method for detecting the presence of hemoglobin in a biological sample. More particularly, the present invention provides a device and method for detecting the presence of blood in a biological sample and still more particularly, the presence of blood in a fecal sample as an indicator of upper or lower gastrointestinal tract bleeding. The method of the present invention is useful, inter alia, for the diagnosis of gastrointestinal tract diseases which can be detected by detecting intestinal bleeding.

BACKGROUND OF THE INVENTION

Bleeding into the bowel is currently the best early indicator of bowel cancer (also know as colorectal cancer). Testing for symptoms of bleeding into the bowel is usually achieved by screening stools for the presence of blood. This test is often referred to as fecal occult blood testing (referred to as "FOBT").

Chemical tests are most widely used for FOBT. These tests typically require stool to be applied to paper impregnated with a chromogen indicator, such as guaiac or 3,3',5,5'-tetramethylbenzidine (TMB), which changes color on oxidation. When developer solution is added to the paper, a blue color develops with a positive result. Guaiac tests have the advantage of being inexpensive and easy to perform, but are less accurate (not specific for human blood) and less sensitive than desirable. Nevertheless, several international studies have shown that screening patients with these tests can save lives through the early detection of pre-cancerous and cancerous lesions. The commonly used guaiac tests detect the heme of hemoglobin, and as this is relatively resistant to breakdown in the small intestine, these tests may detect bleeding anywhere within the intestinal tract. For colorectal cancer screening this may be a disadvantage as these tumors are confined to the large intestine.

Recently, more sensitive and specific immunological tests (e.g. immunochromatographic tests) have been developed that have the potential to improve the accuracy of detecting blood in screening for colorectal cancer. These tests typically detect the globin protein of hemoglobin, a protein that does not survive passage through the upper gastrointestinal tract. A positive immunological test therefore indicates lower gastrointestinal bleeding. In common with all immunologically based tests, however, these tests are subject to a "prozone" or "high dose hook" effect, where at high levels of analyte, the test may be inhibited to the extent that heavy bleeding may be missed.

Heme from hemoglobin has a pseudoperoxidase activity that catalyses the breakdown of peroxide substrates and the release of oxygen. The released oxygen may be detected by suitable chromogenic indicators such as guaiac and tetramethylbenzidine (TMB) which change color on oxidation. Fecal Occult Blood Tests (FOBTs) detect intestinal bleeding by use of this reaction to detect heme from the hemoglobin of red blood cells, and a variety of formats for such tests are known in the art (see, for example, U.S. Pat. Nos. 3,996,007; 4,225,557; 4,789,629; 5,064,766; 5,100,619; 5,106,582; 5,171,528; 5,171,529 and 5,182,191). Typically, FOBTs involve smearing a stool sample on guaiac-impregnated paper and adding a developer solution containing peroxide. If heme is present, a blue color develops on or around the stool specimen. The disadvantages of these tests include:

the stool sample may also contain peroxidases or pseudoperoxidases from ingested foods and these may cause a (false) positive reaction in the absence of human blood from the intestinal tract;

heme from ingested meat may also cause a false positive reaction;

the blue color developed with a positive test must be read against a dark background of stool, so that at lower heme concentrations the result may be equivocal;

with a positive result, color diffuses away from the stool sample, becomes weaker in intensity, and may fade out (the transitory nature of the color change may make also make interpretation of the test result difficult or unreliable);

the developer solution, containing peroxide and other reagents, can interfere with immunochemical tests that may otherwise be used in conjunction with this test for differentiation between upper and lower gastrointestinal bleeding (see, for example, International Patent Publication WO 00/29852, Enterix Inc., combining a chromogen test to detect any intestinal bleeding and an immunochemical test to detect lower intestinal bleeding only).

FOBTs have also been described that have a peroxide reagent such as cumene hydroperoxide dried in a paper matrix (see, for example, Lam, U.S. Pat. No. 4,071,318). In this case, the test paper can be added directly to water and will develop color if heme is present in the water. These FOBTs are typically added to a toilet bowl containing a stool after a bowel movement in order to detect blood released from the stool into the water. The disadvantages of these tests include:

blood on, or in, the stool may not diffuse into the water in sufficient concentration to allow detection;

the test must be read against a background of stool and toilet paper, making interpretation difficult;

the tests may also be subject to interference from dietary heme or peroxidases if there is direct contact between the stool and test paper;

the undeveloped test papers must be stored after manufacture in desiccated conditions to prevent breakdown of the peroxide reagent and development of color in the test paper.

SUMMARY OF THE INVENTION

Throughout this specification and the claims which follow, unless the context requires otherwise, the word "comprise", and or variations such as "comprises" or "comprising", will be understood to imply the inclusion of a stated integer or step or group of integers or steps but not the exclusion of any other integer or step or group of integers or steps.

In one aspect, the present invention provides a device for use in the detection of hemoglobin in a biological sample, particularly a fecal sample, comprising a carrier matrix which includes:

(i) a sample application region for receipt of said biological sample;

(ii) a substrate region in liquid-conductive communication with, or combined with, the sample application region and having a pseudoperoxidase substrate applied thereto or impregnated therein, said pseudoperoxidase substrate comprising a peroxide or hydroperoxide reagent; and (iii) an indicator region in liquid-conductive communication with, or combined with, the substrate region and having an indicator applied thereto or impregnated therein, said indicator producing a detectable response in the presence of heme and said pseudoperoxidase substrate.

In one embodiment of this aspect of the invention, the sample application region and the substrate region may be combined into a single, combined sample application/substrate region having the pseudoperoxidase substrate applied thereto or impregnated therein. In the preferred embodiment, however, the sample application region and the substrate region are separate regions of the carrier matrix which are in liquid-conductive communication.

In another embodiment, the substrate region and the indicator region may be combined into a single, combined substrate/indicator region having both the pseudoperoxidase substrate and the indicator applied thereto or impregnated therein. Preferably, however, the substrate region and the indicator region are separate regions of the carrier matrix which are in liquid-conductive communication.

In another aspect, the present invention provides a method for the detection of hemoglobin in a biological sample, particularly a fecal sample, comprising the steps of:

(i) applying said biological sample to a sample application region of a carrier matrix which comprises said sample application region, a substrate region and an indicator region;

(ii) contacting said biological sample with the substrate region wherein said sample is contacted with a pseudoperoxidase substrate comprising a peroxidase or hydroperoxidase reagent; and (iii) contacting said sample and pseudoperoxidase substrate with the indicator region wherein said sample and substrate are contacted with an indicator which produces a detectable response in the presence of heme and said pseudoperoxidase substrate.

In one embodiment of this aspect of the invention, the biological sample may be contacted with the pseudoperoxidase substrate in a single, combined sample application/substrate region of the carrier matrix, before permitting or causing flow of the sample and substrate to the indicator region. In a preferred embodiment, however, the sample application region and the substrate region are separate regions of the carrier matrix which are in liquid-conductive communication, and the biological sample is applied to the sample application region before permitting or causing flow of the sample to the substrate region.

In another embodiment the biological sample may be contacted with the pseudoperoxidase substrate and indicator in a single, combined substrate/indicator region of the carrier matrix, by permitting or causing flow of the sample from the sample application region to the substrate/indicator region. In a preferred embodiment, however, the substrate region and the indicator region are separate regions of the carrier matrix which are in liquid-conductive communication, and the biological sample is applied to the sample application region before permitting or causing flow of the sample to the substrate region, and then permitting or causing flow of the sample and substrate to the indicator region.

In a particularly preferred embodiment, the device and method of the present invention may combine the detection of heme in a biological sample as broadly outlined above, with an immunochemical test for the detection of globin, thereby providing a dual test for differentiation between upper and lower gastrointestinal tract bleeding which is particularly useful for the detection of lower gastrointestinal tract diseases such as colorectal cancer.

In this preferred embodiment, the carrier matrix of the device as broadly described above further comprises:

(iv) a second substrate region in liquid-conductive communication with the sample application region and having a detectable antiglobin immunointeractive molecule applied thereto or impregnated therein, said immunointeractive molecule forming a detectable globin-antiglobin complex in the presence of globin; and (v) a detection region in liquid-conductive communication with the second substrate region and having an anti-globin immunointeractive molecule immobilized therein, said immobilized immunointeractive molecule immobilizing said detectable globin-antiglobin complex.

Similarly, in this preferred embodiment, the method of the present invention as broadly described above further comprises the steps of:

(vi) contacting said biological sample with a second substrate region wherein said sample is contacted with a detectable antiglobin immunointeractive molecule to form a detectable globin-antiglobin complex in the presence of globin; and (vii) contacting said detectable globin-antiglobin complex with a detection region wherein said detectable globin-antiglobin complex is contacted with an immobilized anti-globin immunointeractive molecule to immobilize said detectable globin-antiglobin complex.

Preferably, the biological sample is permitted or caused to flow from the sample application region to the second substrate region which is in liquid-conductive communication with the sample application region, and the detectable globin-antiglobin complex is permitted or caused to flow from the second substrate region to the detection region which is in liquid-conductive communication with the second substrate region.

DETAILED DESCRIPTION OF THE INVENTION

The present invention provides an improved test format for the detection of hemoglobin which is particularly suitable for the detection of hemoglobin as an indicator of intestinal bleeding. The format is also designed to be compatible with immunochemical tests for the detection of globin so that a dual test for differentiation between upper and lower intestinal bleeding is feasible.

The invention involves the use of lateral flow of a liquid sample (suspected of containing blood) from a point of application through one or more regions containing the reagents required for detection of the heme. The lateral flow layout of the components of the test format has the following advantages:

the color produced with a positive result accumulates as the flow reaches the end of the carrier matrix, concentrating the color and facilitating the ease of reading;

the color of a positive reaction is free of any fecal or other obscuring background material;

dietary contaminants, such as heme from meat or peroxidases from food, are diluted on lateral flow, in many cases to below their threshold detection level;

the sample application region may contain enhancing agents that promote accurate and sensitive detection of the heme by the downstream test components;

incompatible or mutually unstable components or reagents (e.g. substrate and indicator reagents) may be located in separate regions, allowing long-term storage without special manufacturing or storage precautions;

as all reagents can be impregnated in the separate regions, water, water/ethanol mixtures or any other inert reagent may be used for the test development;

the chromogenic heme test (which detects any intestinal bleeding) may therefore be combined with an immunochemical test (which is specific for lower intestinal bleeding) so as to allow for discrimination between upper and lower intestinal bleeding on the one test sample.

The present invention provides a test device for use in the detection of hemoglobin in a biological sample, particularly a fecal sample, comprising a carrier matrix which includes:

(i) a sample application region for receipt of said biological sample;

(ii) a substrate region in liquid-conductive communication with, or combined with, the sample application region and having a pseudoperoxidase substrate applied thereto or impregnated therein, said pseudoperoxidase substrate comprising a peroxide or hydroperoxide reagent; and (iii) an indicator region in liquid-conductive communication with, or combined with, the substrate region and having an indicator applied thereto or impregnated therein, said indicator producing a detectable response in the presence of heme and said pseudoperoxidase substrate.

The invention also provides a test method for the detection of hemoglobin in a biological sample, particularly a fecal sample, comprising the steps of:

(i) applying said biological sample to a sample application region of a carrier matrix which comprises said sample application region, a substrate region and an indicator region;

(ii) contacting said biological sample with the substrate region wherein said sample is contacted with a pseudoperoxidase substrate comprising a peroxidase or hydroperoxidase reagent; and (iii) contacting said sample and pseudoperoxidase substrate with the indicator region wherein said sample and substrate are contacted with an indicator which produces a detectable response in the presence of heme and said pseudoperoxidase substrate.

Reference to a "biological sample" should be understood as a reference to any sample of biological material derived from an animal such as, but not limited to, faeces, mucus, urine, biopsy specimens and fluid which has been introduced into the body of an animal and subsequently removed such as, for example, the saline solution extracted from the lung following lung lavage or the solution retrieved from an enema wash. The biological sample which is tested according to the method of the present invention may be tested directly or may require some form of treatment prior to testing. For example, a biopsy sample may require homogenisation prior to testing. Further, to the extent that the biological sample is not in liquid form, (for example it may be a solid, semi-solid or dehydrated liquid sample) it may require the addition of a reagent, such as a buffer, to mobilize the sample. The mobilizing reagent may be mixed with the biological sample prior to application of the sample to the carrier matrix or the reagent may be applied to the sample after the sample has been applied to the carrier matrix. The use of a mobilizing reagent may also be required to facilitate lateral flow (wicking) of the sample along the carrier matrix. Preferably, the biological sample is a gastrointestinal sample. By "gastrointestinal sample" is meant any sample which is derived from the gastrointestinal tract. For example, feces, mucus (for example the mucus from a rectal mucus swab), enema wash solution or a gastrointestinal tract biopsy sample. Most preferably, the biological sample is a stool sample, or a sample of water from a toilet bowl containing a stool.

The term "animal" as used herein includes a human, primate, livestock animal (e.g. sheep, pig, cow, horse, donkey), laboratory test animal (e.g. mouse, rat, rabbit, guinea pig) companion animal (e.g. dog, cat), captive wild animal (e.g. fox, kangaroo, deer), aves (e.g. chicken, geese, duck, emu, ostrich), reptile or fish. Preferably, however, the animal is a human.

Preferably, the carrier matrix used in forming the test device of the present invention is in the form of a test strip of a suitable material which permits liquid-conductive communication between the various zones or regions of the matrix. A particularly preferred material is one which allows capillary flow, such as an open-celled, chemically inert matrix, with porous plastics material, filter paper and glass fiber being preferred. Other suitable materials are well known in the art (see, for example, Lam U.S. Pat. No. 4,071,318), and are intended to be encompassed within the scope of the present invention.

Preferably, the sample application region of the carrier matrix includes an absorbent pad such as a non-woven polyester pad which is impregnated with a reagent to lyse any red blood cells present in the sample so as to release hemoglobin, to minimise binding to the pad and to promote sample flow from the pad. Particularly suitable lysis reagents are detergents (such as Triton X100). After the sample is applied to the pad, a mobilizing agent such as water or a water/ethanol mixture can be applied to the pad to mobilize any heme (and globin) in the sample and permit or cause the sample to flow or wick by capillary action through the carrier matrix to the substrate region(s).

The pseudoperoxidase substrate which is present in the substrate region comprises a peroxidase or hydroperoxidase reagent as the main reagent, optionally together with supplementary stabilizers, enhancers and accelerators which are known to persons skilled in the art. Suitable peroxidase or hydroperoxidase reagents include, for example, t-butyl hydroperoxide, cumene hydroperoxide, diisopropylbenzene hydroperoxide, 2,5-dimethylhexane-2,5-dihydroperoxide, paramenthane hydroperoxide or mixtures thereof. Of these, cumene hydroperoxide has been found to be most preferable. Suitable stabilizing and enhancing agents are also well known in the art, and include borate esters such as trimethanolamine borate, triethanolamine borate and tri(n-propanol) amine borate, as stabilizing agents, and 6-methoxyquinoline as an enhancing agent (see Lam U.S. Pat. No. 4,071,318).

The indicator which is present in the indicator region to produce a detectable response in the presence of heme and the pseudoperoxidase substrate is preferable a chromogen such as guaiac or a benzidine compound, for example benzidine, o-tolidine, 3,3',5,5'-tetramethylbenzidine (TMB), 2,7-diaminofluorene, or mixtures of these in varying proportions. Once again, stabilizing agents and/or enhancing agents which are well known to persons skilled in the art may be included in the indicator.

Preferably, in carrying out the method of the present invention, the sample is applied to an absorbent sample pad in the sample application region where any red blood cells in the sample are lysed by detergent or other lysis reagent in the sample pad to release the hemoglobin. The sample is then permitted or caused to flow by capillary action from the sample pad to the substrate region using water or water/ethanol as a mobilizing agent to develop the test and to solubilize dried pseudoperoxidase substrate (such as cumene peroxide) and other stabilizing and enhancing reagents located in this substrate region. The sample and pseudoperoxidase substrate are then permitted or caused to flow by capillary action to the indicator region where the presence of heme in the sample is detected by a reaction with the chromogen such as guaiac or TMB, resulting in a detectable color change.

In a preferred aspect of the invention, the detection of heme in the biological sample, as described in detail above, is combined with an immunochemical test in a "dual test" which allows differentiation of upper and lower intestinal bleeding in the test sample.

Accordingly, in this aspect, the present invention provides a test device as broadly described above in which the carrier matrix further comprises:

(iv) a second substrate region in liquid-conductive communication with the sample application region and having a detectable antiglobin immunointeractive molecule applied thereto or impregnated therein, said immunointeractive molecule forming a detectable globin-antiglobin complex in the presence of globin; and (v) a detection region in liquid-conductive communication with the second substrate region and having an anti-globin immunointeractive molecule immobilized therein, said immobilized immunointeractive molecule immobilizing said detectable globin-antiglobin complex.

The carrier matrix of the test device of the present invention may also comprise additional regions to the regions specifically described above. For example, the device may also comprise an absorbent pad or pads located after the indicator region and/or detection region to draw the mobilising liquid front from the sample application region through the respective regions in liquid-conductive communication with each other in order to develop the tests.

In the preferred aspect, the present invention also provides a method as broadly outlined above which further comprises the steps of:

(vi) contacting said biological sample with a second substrate region wherein said sample is contacted with a detectable antiglobin immunointeractive molecule to form a detectable globin-antiglobin complex in the presence of globin; and (vii) contacting said detectable globin-antiglobin complex with a detection region wherein said detectable globin-antiglobin complex is contacted with an immobilized antiglobin immunointeractive molecule to immobilize said detectable globin-antiglobin complex.

Reference throughout this specification to "immunointeractive molecule" should be understood as a reference to any molecule comprising an antigen binding portion or a derivative of said molecule. Examples of molecules contemplated by this aspect of the present invention include, but are not limited to, monoclonal and polyclonal antibodies (including synthetic antibodies), hybrid antibodies, humanised antibodies, catalytic antibodies) and T cell antigen binding molecules. Preferably, said immunointeractive molecule is an antibody.

Full details of suitable detectable antiglobin immunointeractive molecules present in the second substrate region, and of suitable immobilised antiglobin immunointeractive molecules present in the detection region, are set out in International Patent Publication No. WO 00/29852, in the name of Enterix Inc., the contents of which are incorporated herein by reference.

"Detecting" the formation of a globin-antiglobin complex may be by any convenient method which will be known to those skilled in the art. In the preferred method of the invention described herein, the antiglobin antibody which becomes resuspended by the wicking biological sample front is complexed with colloidal gold. As the globin-antiglobin/colloidal gold complex is trapped by the antiglobin capture antibody impregnated in the detection region of the carrier matrix, the colloidal gold becomes visible as a pink band due to its increasing concentration during trapping of the complex at this point. Alternatively, the antiglobin antibody may be radio-labeled, or enzymatically labeled such that upon addition of a substrate a color change is observed if globin is present.

In one preferred embodiment of the "dual test" aspect of the present invention, detection of heme is carried out as described in detail above. Detection of globin in the biological sample is carried out using a chromatographic test strip which comprises a second substrate region and a detection region. The second substrate region is an area of immobilized antiglobin antibody coupled to colloidal gold particles which are re-suspendible by a passing liquid front, while the detection region is an area of immobilized antiglobin capture antibody.

In this preferred aspect of the invention, the biological sample which is applied to the sample application region flows or wicks to the second substrate region and at this region, the globin component of any hemoglobin which is present in the sample is bound by the antiglobin antibody coupled to the colloidal gold particles. The passing biological sample front re-suspends these antibodies and the globin-antiglobin complex flows or wicks to the detection region where the globin component of any hemoglobin present in the sample and bound in the globin-antiglobin complex becomes bound to the immobilized antiglobin capture antibody where it is detectable.

In this dual test aspect, the present invention may be used to diagnose gastrointestinal tract bleeding by analysing fecal samples for the presence of blood. Without limiting the present invention to any one theory or mode of action, the chromogen test will positively identify bleeding from any part of the gastrointestinal tract (that is, both the upper and lower regions of the tract) since it detects the heme component of hemoglobin and heme is relatively resistant to breakdown in the small intestine (the upper gastrointestinal tract). The globin component of hemoglobin however, does not survive passage through the upper gastrointestinal tract. A positive globin result in a fecal sample therefore indicates that bleeding has occurred in the lower gastrointestinal tract. Accordingly, by applying a combined dual immunological and non-immunological based test, it is possible to differentiate between upper and lower gastrointestinal tract bleeding wherein a positive heme result together with a negative globin result indicates upper gastrointestinal tract bleeding, and a positive heme result together with a positive globin result indicates lower gastrointestinal tract bleeding. This is of particular importance, for example to the diagnosis of colorectal cancer, the symptoms of which include lower gastrointestinal tract bleeding.

Further features of the test device and method of the present invention are more fully described below with reference to the accompanying drawing.

BRIEF DESCRIPTION OF THE DRAWINGS

FIG. 1 is a schematic representation of a "dual test" device in accordance with a preferred embodiment of the present invention.

FIG. 2A shows a FOBT test strip, and FIG. 2B shows a FOBT test strip in housing.

DESCRIPTION OF PREFERRED EMBODIMENTS

Figure 1:
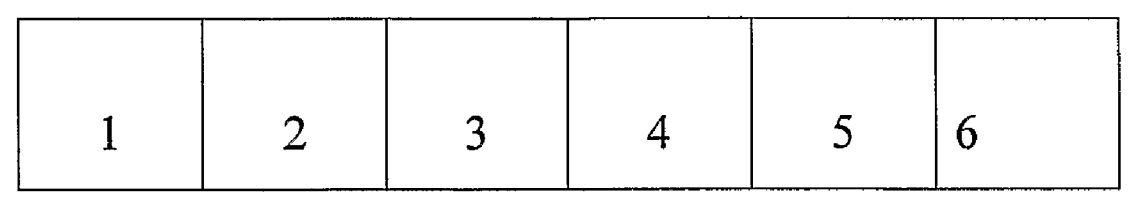
Figure 2:
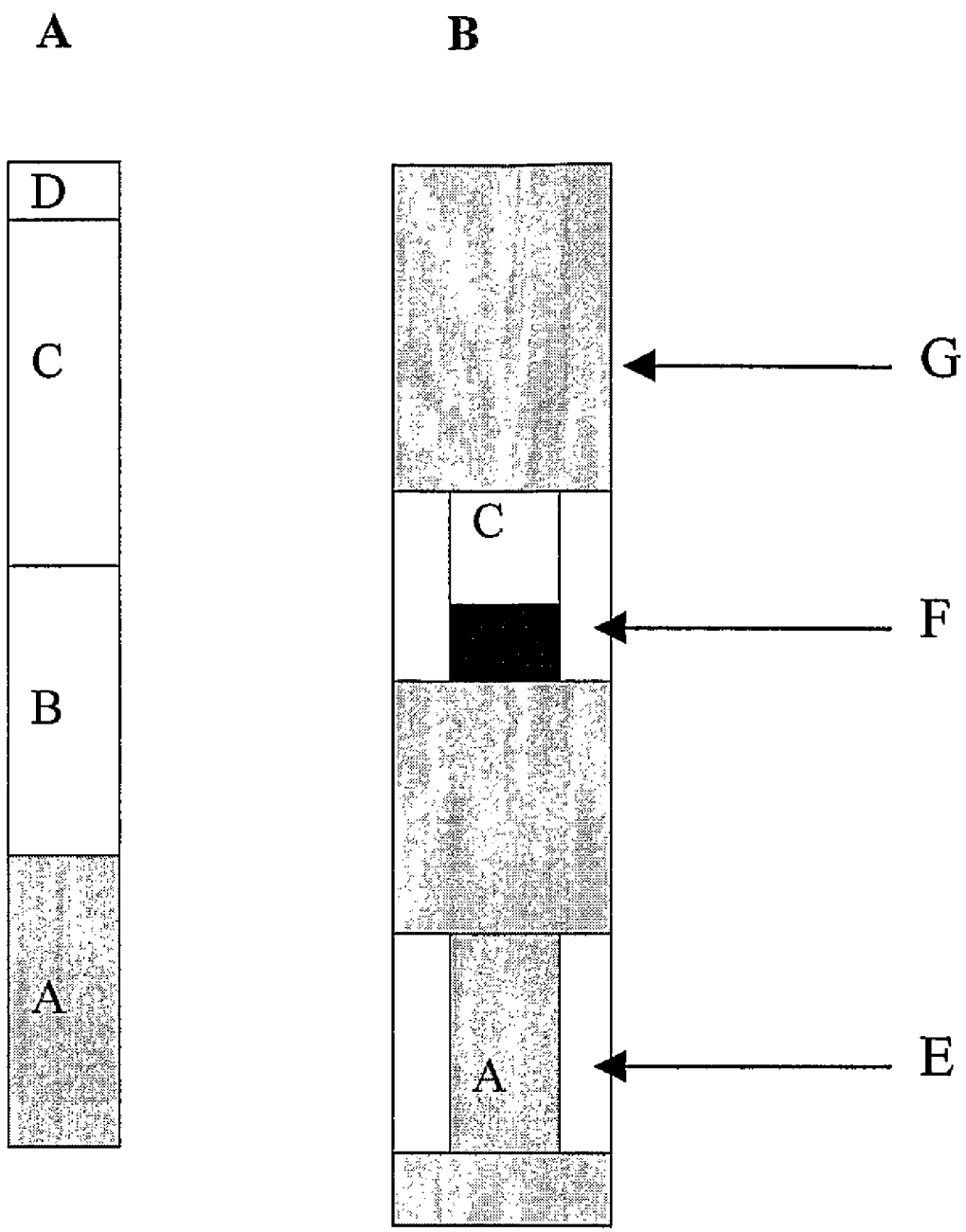
FIGS. 2A and 2B are schematic representations of an alternative device in accordance with the present invention.

FIG. 1 shows schematically a dual test strip format in accordance with the present invention, which comprises the following components in liquid-conductive communication in a single test strip, as follows:
  TMB impregnated indicator paper (1);
  Substrate (e.g. dried cumene peroxide) impregnated paper (2);
  Sample pad (e.g. non woven polyester impregnated detergent, e.g. with Triton X100) (3);
  Conjugate pad (e.g. gold labeled anti-human globin antibodies) (4);
  Solid phase (e.g. nitrocellulose membrane with immobilized anti-human globin antibody line and a procedural control line) (5);
  Absorbent pad (6).

Components 1, 2 and 3 constitute the basic components of the test device of the present invention. If desired, components 1 and 2 may be combined, provided precautions are observed to provide storage stability of the various reagents. Components 4, 5 and 6 constitute the additional components of the preferred embodiment of this invention which includes an immunochemical test strip for detecting human globin as an indicator of lower intestinal bleeding.

Sample, for example, a stool sample from a digital rectal examination (DRE), or a water sample taken from around a stool in a toilet bowl, is applied to the sample pad 3, where any red blood cells are lysed by the detergent impregnated in the sample pad, and developer solution is added. The developer solution may be water, or may include buffer, ethanol and other reagents that assist the reactions and that are compatible with both types of test. From the sample pad, the developer solution mobilizes any hemoglobin released from red blood cells and moves laterally from pad 3 through the flanking regions of the test strip in both directions.

Heme, if present, mixes with the pseudoperoxidase substrate in substrate region 2 and then mixes with the chromogenic indicator in indicator region 1, where the color accumulates at the end of region 1.

Globin, if present, is detected in the detection region 5 after labeling with the gold-labeled antibody conjugate in substrate region 4. Excess developer solution and other reagent accumulate in the absorbent pad 6.

Clearly, the dual test strip illustrated in FIG. 1 may be encased in a housing adapted for receipt of the sample on pad 3, with provision (e.g. windows or similar apertures) for visual, or instrumented, detection of the results in indicator region 1 and detection region 5.

EXAMPLE 1

Reagent solutions were prepared based on Lam, U.S. Pat. No. 4,071,318, as follows:

| Solution A: | |
|---|---|
| Water | 10 mL |
| Trisodium citrate | 213 mg |
| Citric acid | 147 mg |
| EDTA | 6.7 mg |

| -continued | |
|---|---|
| Sodium lauryl sulfate | 67 mg |
| Methyl sulfone | 667 mg |
| Acetone | 1.67 mL |
| Solution B (indicator): | |
| Tetra methyl benzidine (TMB) | 26.7 mg dissolved in |
| Dimethylsulfoxide | 1.67 mL |
| Solution C (substrate): | |
| Cumene hydroperoxide | 133.3 mg |
| 6-methoxy quinoline | 33.3 mg |
| Triethanolamine borate | 667 mg |
| Solution A | 5 mL |

To prepare reactive paper, solutions A, B and C were mixed just before use and added to Whatmans # 1 paper until the paper was soaked. The impregnated reactive paper was hung vertically to drain excess liquid and dried in a warm air current for approximately 30 minutes. The activity of the reactive paper was confirmed by diluting blood obtained from a finger prick in water and adding the dilutions to small pieces of the reactive paper. A 1/100 dilution gave an instant strong blue-green color, 1/1000 produced a strong blue color, 1/10,000 produced a slower developing green color, whereas the 1/100,000 dilution produced a borderline pale blue after 1-2 minutes. Water alone added to the reactive paper produced no color, even when left until dry.

The reactive paper was tested in a device constructed as shown in FIG. 2A (FOBT test strip) and 2B (FOB test strip in housing). FOBT test strips were prepared by laminating the pads A, B, C and D as shown in FIG. 2A with double sided adhesive (3M #465, 3M MN) to a white plastic (high impact polystyrene)backing (D) and cutting the laminate into test strips approximately 10 mm wide. The test strips were then placed in a waterproof cardboard housing (G) with a port (E) for sample and reagent addition and a window (F). For ease of reading the test result, the interface between pads B and C was located centrally in the observation window (F) of the test housing (G).

In the test strips shown in FIG. 2A:

| | |
|---|---|
| Pad A: | Non-woven polyester fabric (e.g. Ahlstrom 6613, Ahlstrom, PA) impregnated with 0.1% Triton X-100 detergent. |
| Pad B: | Reactive paper |
| Pad C: | White plastic barrier tape. |
| Pad D | Backing. |

In this test strip, pad A is the sample application pad, and pad B is a combined substrate/indicator region.

Blood diluted 1/1000 in water was applied to pad A of the test strip of FIG. 2A via the sample port (E) followed by three drops of water. The liquid migrated from pad A via pad B so that within 25 seconds a strong blue color accumulated at the end of pad B against the white impermeable barrier of pad C. Water alone added to Pad A produced no color in the test window.

EXAMPLE 2

Figure 3:
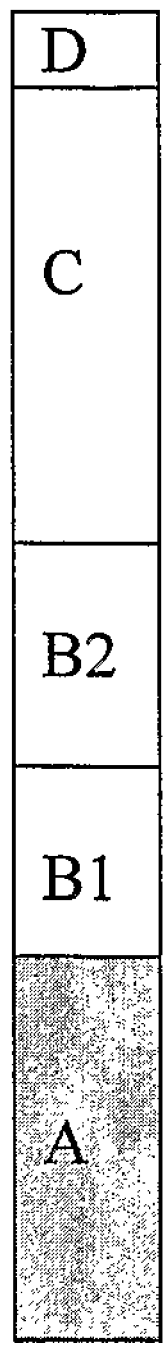
FIG. 3 is a schematic representation of a further alternative device in accordance with the present invention.

For long term stability of the FOBT test strip, the substrate and indicator regions were prepared and laminated separately in a test strip constructed as shown in FIG. 3 as a modification of the test strip shown in FIG. 2A.

In the test strip of FIG. 3, pad A is the sample application pad, pad B1 is the substrate region and pad B2 is the indicator region. The test strip is prepared as described in Example 1, using substrate paper B1 and indicator paper B2 instead of reactive paper B, as follows:

Substrate paper B1: Solution C was prepared, soaked into Whatman's #1 filter paper and drip-dried.

Indicator paper B2: Solutions A and B were mixed, soaked into Whatman's #1 filter paper and drip-dried.

Both papers B1 and B2 were then fully dried in forced air at low heat.

10 µL of human blood diluted 1/1000 in water was added to pad A of the test strip of FIG. 3 followed by three drops of a reagent comprised of Bovine serum albumin (3%), Ethanol (10%) and sodium azide in 40 mM sodium borate buffer, pH 8.5. Blue color accumulated at the interface of membrane B2 and C. No color developed with a water sample alone.

In an alternative embodiment, the substrate Solution C may be incorporated into pad A during manufacture, and pad B1 omitted from the test strip.

EXAMPLE 3

FOBT test strips, as described for Example 1, were used in combination with commercially available immunochemical (ICT) test strips (InSure FIT, Enterix Inc., NJ). These ICT test strips are used for detection of human globin as an indicator of lower intestinal bleeding.

The two test strips (FOBT and ICT) were laid end to end so that the origin of the ICT strip was in contact with pad A of the test strip as described in Example 1. 10 µL of a 1/1000 dilution of human blood in water was added to pad A, followed by four drops of the reagent described in Example 2. The sample migrated in both directions from the point of application and both tests developed a positive result. When water containing diluted blood taken from a beef sample was tested in the same manner it gave a positive result with the FOBT test strip (i.e., positive for hemoglobin), but a negative result with the ICT test (i.e., negative for human globulin). Water alone gave a negative result with both tests.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

The invention claimed is:

1. A device for the detection of hemoglobin in a biological sample, comprising a carrier matrix which includes:
   (i) a sample application region for receipt of said biological sample;
   (ii) a first substrate region in liquid-conductive communication with, or combined with, the sample application region and having a pseudoperoxidase substrate loaded therein in a dried state; said pseudoperoxidase substrate comprising a peroxide or hydroperoxide reagent; and
   (iii) a first indicator region in liquid-conductive communication with, or combined with, the first substrate region and having an indicator applied thereto or impregnated therein, said indicator capable of producing a detectable response in the presence of heme and said pseudoperoxidase substrate;
   (iv) a second substrate region in liquid-conductive communication with the sample application region and having a detectable anti-globin immunointeractive molecule applied thereto or impregnated therein, said immunointeractive molecule forming a detectable globin-antiglobin complex in the presence of globin; and
   (v) a second indicator region in liquid-conductive communication with the second substrate region and having an anti-globin immunointeractive molecule immobilized therein, said immobilized immunointeractive molecule immobilizing said detectable globin-antiglobin complex.

2. The device of claim 1, wherein the sample application region and the first substrate region are combined in a combined sample application/substrate region of the carrier matrix.

3. The device of claim 1, where the sample application region and the first substrate region are separate regions of the carrier matrix which are in liquid-conductive communication.

4. The device of claim 1, wherein the first substrate region and the first indicator region are combined in a combined substrate/indicator region of the carrier matrix.

5. The device of claim 1, wherein the first substrate region and the first indicator region are separate regions of the carrier matrix which are in liquid-conductive communication.

6. A device for the detection of hemoglobin in a biological sample comprising:
   (i) a centrally disposed sample application region,
   (ii) a first laterally disposed test region, and
   (iii) a second laterally disposed test region,
      wherein each test region is in direct liquid-conductive communication with said sample application region, and
      wherein said first test region comprises a substrate region having a pseudoperoxidase substrate loaded therein in a dried state, and an indicator region having an indicator applied thereto or impregnated therein, said indicator capable of producing a detectable response in the presence of heme and said pseudoperoxidase substrate,
      wherein said second test region comprises a substrate region having a detectable antiglobin immunointeractive molecule applied thereto or impregnated therein, said immunointeractive molecule forming a detectable globin-antiglobin complex in the presence of globin; and a detection region having an antiglobin immunointeractive molecule immobilized therein, wherein said immunointeractive molecule is capable of immobilizing said detectable globin-antiglobin complex.

7. The device of claim 1, wherein said detectable anti-globin immunointeractive molecule in said second substrate region is in a dried state after being applied thereto or impregnated therein.

8. The device of claim 1, wherein the carrier matrix comprises a centrally-disposed sample application region and the first substrate region and the second substrate region are each laterally disposed from the sample application region.

9. The device of claim 8, wherein the substrate region and the indicator region are combined in a combined substrate/indicator region of the carrier matrix.

10. The device of claim 8, wherein the first substrate region and the first indicator region are separate regions of the carrier matrix which are in liquid-conductive communication.

* * * * *